United States Patent [19]
Hartmann et al.

[11] 4,383,894
[45] May 17, 1983

[54] REMOVAL OF ORGANIC IODINE COMPOUNDS FROM ACETALDEHYDE

[75] Inventors: Horst Hartmann, Boehl-Iggelheim; Waldhelm Hochstein, Freinsheim; Gerd Kaibel, Lampertheim; Franz-Josef Mueller, Wachenheim, all of Fed. Rep. of Germany

[73] Assignee: BASF Aktiengesellschaft, Ludwigshafen, Fed. Rep. of Germany

[21] Appl. No.: 316,301

[22] Filed: Oct. 29, 1981

[30] Foreign Application Priority Data

Nov. 29, 1980 [DE] Fed. Rep. of Germany ....... 3045105

[51] Int. Cl.³ .............................................. B01D 3/36
[52] U.S. Cl. ........................................ 203/70; 568/492
[58] Field of Search .................... 568/492; 203/69, 70

[56] References Cited

U.S. PATENT DOCUMENTS 2,452,797 11/1948 Smith ................................. 203/70
2,707,165 4/1955 MacLean ........................... 568/492
3,062,889 11/1962 Murphy .............................. 568/492

FOREIGN PATENT DOCUMENTS 593719 3/1960 Canada ............................... 568/492

Primary Examiner—Frank Sever
Attorney, Agent, or Firm—John H. Shurtleff

[57] ABSTRACT

A process for separating off organic iodine compounds from acetaldehyde by subjecting the acetaldehyde to azeotropic distillation with a hydrocarbon boiling at from 25° to 55° C. under atmospheric pressure.

6 Claims, 1 Drawing Figure

Me = methanol
Ald = acetaldehyde
Ald-Me = acetaldehyde dimethylacetal
Me-Ac = methyl acetetate
I = methyliodide
IP = isopentane
o = others
( ) = minor amounts

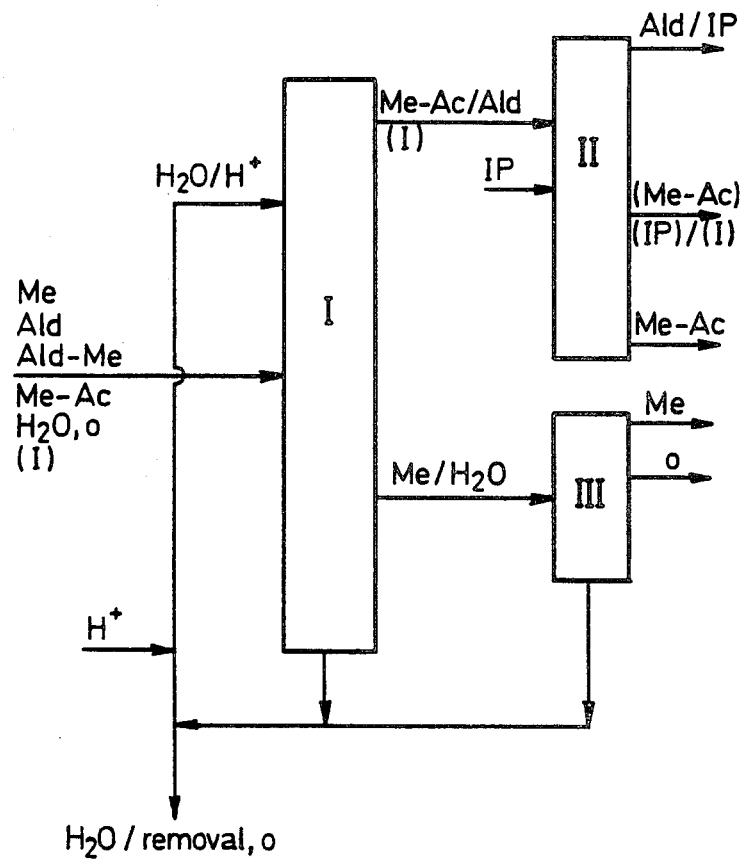
Me= methanol
Ald= acetaldehyde
Ald-Me= acetaldehyde dimethylacetal
Me-Ac= methyl acetetate
I= methyliodide
IP= isopentane
o = others
( ) = minor amounts

REMOVAL OF ORGANIC IODINE COMPOUNDS FROM ACETALDEHYDE

The present invention relates to a novel process for removing organic iodine compounds, such as, in particular, methyl iodide, from acetaldehyde.

Acetaldehyde contaminated by organic iodine compounds, in particular methyl iodide, is obtained by so-called homologization of methanol by means of a catalyst system comprising carbonyl complexes of metals of group VIII of the Periodic Table of the elements and iodine compounds as activators. Details of this reaction, with which the present invention is not concerned, are in the monograph by Falbe "Chemierohstoffe aus Kohle," Georg-Thieme Verlag, 1977, page 329 et seq., and in the original publications quoted therein.

If iodides are used as activators, the crude acetaldehyde obtained after the catalyst metals have been separated off is always contaminated by small amounts of methyl iodide and other organic iodine compounds which are formed during the homologization reaction.

As a rule, the usually unavoidable substantial removal of iodo-organic impurities from organic compounds presents considerable difficulties. Furthermore, in the present case, the generally known chemical methods, such as treatment with alkali, reduction or oxidation, are excluded a priori if considerable losses of acetaldehyde, which is extremely sensitive to such reactions, are not to be tolerated. On the other hand, fractionation is impossible because acetaldehyde and methyl iodide are virtually inseparable.

The process disclosed in German Laid-Open Application DOS No. 2,940,751 for removing organic iodine compounds from carbonylation products of methyl acetate, in which the iodine of the organic iodine compounds is converted into non-volatile alkali metal iodides at elevated temperatures by means of alkali metal acetates, is not only unsatisfactory because it is technologically cumbersome, but also cannot successfully be applied to the purification of acetaldehyde because of the sensitivity of acetaldehyde to alkali.

It is an object of the present invention to free acetaldehyde from organic iodine compounds in a simpler and more effective manner than that used hitherto.

We have found that this object is achieved and that organic iodine compounds can elegantly be removed from acetaldehyde if the acetaldehyde is subjected to azeotropic distillation with a hydrocarbon having a boiling point, under atmospheric pressure, of from 25° to 55° C.

Suitable hydrocarbons are n-pentane, isopentane (methylbutane), cyclopentane and 2,2-dimethylbutane.

Since isopentane is particularly suitable for the purpose of the invention, the invention will be illustrated for this case, in the text which follows. Apart from somewhat different compositions of the azeotropic mixtures and somewhat different distillation temperatures, the same statements apply to the use of the other hydrocarbons conforming to the above definition.

Since it has been found, surprisingly, that the acetaldehyde/isopentane azeotrope contains only extremely small amounts of iodine compounds, the initial concentration of iodine compounds in the crude acetaldehyde is irrelevant.

In the most important industrial case, that is to say removal of methyl iodide and small amounts of other iodo-organic compounds, which for practical purposes are reckoned as methyl iodide, the azeotrope, which has a boiling point, under atmospheric pressure, of 11° C., is composed of about 25% by weight of acetaldehyde and about 75% by weight of isopentane. This composition remains virtually unchanged as the pressure increases up to about 4 bar. In all cases, the concentration of the methyl iodide in the distillate is below 0.5 ppm.

In practice, a pressure of from 2 bar (boiling point of the azeotrope: 29° C.) to 3 bar (boiling point: 42° C.) is preferred because cooling is easier during the distillation.

The pure acetaldehyde can be isolated by first condensing the acetaldehyde/isopentane azeotrope and then extracting the acetaldehyde therefrom with water in a conventional manner. However, it is also possible for the azeotrope to be taken up in water directly from the gas phase. In both cases, from about 1 to 5 kg of water are required per kilogram of acetaldehyde, depending on the hydrocarbon content which can be tolerated in the acetaldehyde.

The acetaldehyde can then be isolated from the aqueous phase by distillation in a conventional manner.

The azeotropic distillation according to the invention can be carried out in columns of any desired construction, preferably with from 20 to 35 theoretical plates.

In a particularly advantageous embodiment, the process according to the invention is integrated into the process for obtaining acetaldehyde from reaction mixtures resulting from homologization of methanol, according to German Pat. No. 3,019,765 (Patent Application No. P 30 19 765).

In this process for working up the homologization mixtures which, in addition to acetaldehyde, essentially contain acetaldehyde dimethyl acetal, methanol, methyl acetate and water, to give acetaldehyde, (a) the homologization mixture is introduced into the middle section of a column I at a temperature at which the methyl acetate or its azeotropic mixture with methanol, but not the methanol, vaporizes completely, ($b_1$) liquid aqueous acid is fed, in counter-current to the rising vapors, into the top quarter of column I and splits the acetaldehyde dimethyl acetal into acetaldehyde and methanol, or ($b_2$) instead of the aqueous acid, only water is used and the acetal is split by means of a solid acid ion exchanger, (c) a vaporous mixture of methyl acetate and acetaldehyde is taken off at the top of column I and is separated into its components in a column II, (d) a liquid mixture of methanol and water is taken off from the bottom quarter of column I and is separated into its components in a column III, and (e) some of the aqueous acid (embodiment $b_1$) obtained in the bottom of column I or some of the water (embodiment $b_2$) is removed from the system with minor amounts of other products, and the remainder of this aqueous acid or of the water is combined with the water obtained in the bottom of column III, and the aqueous solution is recycled into the top quarter of column I, after addition of an acid.

If the methyl acetate and acetaldehyde are separated according to the invention in the presence of isopentane in process step (c), iodine-free acetaldehyde is obtained directly from a single integrated unit for working up catalyst-free reaction mixtures from the homologization of methanol if this homologization, as is generally the case, has been carried out with iodine compounds as activators. The drawing illustrates this procedure.

In one embodiment of this integrated process, it is also possible to transfer the isolation of the acetaldehyde/isopentane azeotrope to the upper section of column I and to separate off the methyl acetate in a subsidiary stripping column.

In both cases, the methyl iodide passes into the methyl acetate. The mixture obtained can be separated, by distillation in the same apparatus, into an iodine-free fraction and, as a lateral take-off, an iodine-containing and isopentane-containing fraction. The iodine-containing fraction can then be recycled to the homologization stage. A closed iodine circulation in which the iodine compounds do not undergo any conversions is thereby made possible, which is of particular technological advantage.

The process according to the invention is based on the discovery that methyl iodide and other organic iodine compounds can be removed from acetaldehyde by azeotropic distillation with the hydrocarbons defined, independently of how the iodine compounds have come to be in the acetaldehyde.

However, this separation problem has hitherto been of great importance in practice only if the homologization of methanol has been interrupted at the acetaldehyde stage by choosing relatively low conversions and avoiding too high a partial pressure of hydrogen. This partial homologization is usually preferred to complete homologization to give ethanol, since acetaldehyde has more uses than ethanol.

Partial homologization of methanol is generally carried out at from 150° to 200° C. and under a CO partial pressure of from 100 to 200 bar and a $H_2$ partial pressure of from 100 to 200 bar, preferably in the presence of cobalt carbonyl complexes or rhodium carbonyl complexes in which some of the carbonyl can also be replaced by other ligands, such as trialkylphosphines, trialkyl phosphites or triphenylphosphine. The amount of these catalysts, calculated relative to the metal, is from about 0.01 to 0.1 mole % of the methanol. Iodine compounds, such as hydrogen idodie, alkali methal iodides or, in particular, methyl iodide, which always forms regardless of the source of the iodine, greatly favor the homologization reaction and are used in an amount of from about 1.5 to 3 times the molar amount of catalyst metal, so that, in addition to from 30 to 75% by weight of methanol, from 2 to 10% by weight of acetaldehyde, from 8 to 30% by weight of acetaldehyde dimethyl acetal, from 5 to 10% by weight of methyl acetate and from 10 to 20% by weight of water, the reaction product contains from about 0.01 to 0.1% by weight of methyl iodide.

If non-volatile catalysts (eg. rhodium/triphenylphosphine/carbonyl complexes) are used, the reaction mixture can be separated off, and passed to the further processing steps, in the form of a gas. In the case of volatile metal carbonyls, for example dicobalt octacarbonyl, it is necessary first to decompose the catalyst into the corresponding metal salt, for example cobalt acetate, using, for example, air.

If the catalyst-free reaction mixture is first worked up by coarse fractionation to give the crude acetaldehyde, this product contains from about 100 to 500 ppm of methyl iodide. If this operation is followed by batchwise purification by the process according to the invention and a column with from 15 to 30 theoretical plates, which is usually a sufficient number, is used, the methyl iodide concentration at the bottom of the distillation column should not be allowed to rise above from 1 to 2% by weight, so that the methyl iodide partial pressure does not become too high for the separating capacity of such a column.

In the case of the continuous procedure, for example that of the integrated system described above, the problem of too high a concentration of methyl iodide does not arise at any point, since the methyl iodide is continuously removed, due to the very nature of a continuous process.

EXAMPLE 1

A column of 30 mm internal diameter and 80 cm height and packed with metal gauge rings was used as the distillation column. This column, which was operated continuously, under atmospheric pressure, had 28 theoretical plates.

60 g per hour of acetaldehyde, which was contaminated with about 300 ppm of methyl iodide, were fed in at the 8th plate (counted from the bottom). This plate was at about 15° C. 120 g per hour of isopentane were introduced into the column at the level of the 18th plate.

A mixture of 49 g of acetaldehyde and 120 g of isopentane, containing only about 0.5 ppm of methyl iodide, was taken off per hour at the top of the column (11° C.) at a reflux ratio of 5. 11 g per hour of acetaldehyde, contaminated with about 0.16% by weight of methyl iodide, were obtained at the bottom of the column (21° C.).

EXAMPLE 2

This example was carried out under atmospheric pressure in a test apparatus as shown in the figure. All the columns were packed columns. Column I was 2 m high and had an internal diameter of 5 cm and 40 theoretical plates. Column II was 2.50 m high and had an internal diameter of 5 cm and 60 theoretical plates, and column III was 0.8 m high and had an internal diameter of 5 cm and 12 theoretical plates. 300 g per hour of a reaction mixture originating from the homologization of methanol were fed into column I at the level of the 30th theoretical plate (counted from the bottom), which was at 61° C.

The homologization was carried out with a mixture of 50% by volume of hydrogen and 50% by volume of carbon monoxide under 300 bar and at 125° C., in the presence of 0.3% by weight of cobalt as cobalt acetate and about 1% by weight of methyl iodide, based on the contents of the reactor; a methanol conversion of about 26% was maintained. After having been let down, the resulting reaction mixture was aerated to destroy the cobalt complex. The mixture was then distilled from the resulting cobalt salt. This mixture had the following composition: 54% by weight (162 g) of methanol, 7% by weight (21 g) of acetaldehyde, 9% by weight (27 g) of acetaldehyde dimethyl acetal, 7% by weight (21 g) of methyl acetate, 15% by weight (45 g) of water, 6% by weight (18 g) of ethanol, 2% by weight (6 g) of other products and about 30 ppm of methyl iodide.

100 g per hour of 1% strength by weight aqueous sulfuric acid, which also contained a little ethanol and other products, were introduced into column I at the level of the 35th plate (48° C.)

A mixture of 34 g of acetaldehyde, 21 g of methyl acetate, 0.5 g of acetaldehyde dimethyl acetal and 0.1 g of methanol and about 300 ppm of methyl iodide was taken off per hour at the top of the column (29° C.) at a reflux ratio of 5.

This mixture was introduced into column II at the level of the 50th plate (25°–30° C.), and 100 g per hour of isopentane were fed in at the level of the 40th plate.

A mixture of 34 g of acetaldehyde and 99 g of isopentane with a methyl iodide content of less than 10 ppm was taken off per hour at the top of column II at a reflux ratio of 7.

18.5 g per hour of methyl acetate which, in addition to a little methanol and acetaldehyde dimethyl acetal, contained only 30 ppm of methyl iodide, were obtained as the bottom product (58° C.) in column II.

A mixture of 2.5 g of methyl acetate and 1 g of isopentane, containing about 0.4% by weight of methyl iodide, was taken off per hour as a vaporous lateral take-off at the level of the 30th plate of column II.

A vaporous lateral take-off was obtained at the level of the 15th plate (75° C.) in column I and was separated in column III into 181 g of methanol, as the top product, and 64 g of a bottom product consisting of 40 g of water, 18 g of ethanol and 6 g of other products.

This bottom product was combined with the bottom product from column I (110° C.), which consisted of 100 g of aqueous sulfuric acid, after which 64 g of the combined bottom products were removed from the circulation. Further sulfuric acid was then introduced into the circulation in order to keep the acid concentration constant.

We claim:

1. A process for removing organic iodine compounds as an impurity from acetaldehyde, which comprises:
    subjecting the impure acetaldehyde to azeotropic distillation with a hydrocarbon which has a boiling point, under atmospheric pressure, of from 25° to 55° C., said distillation being carried out under conditions of temperature and pressure sufficient to obtain the purified acetaldehyde in the azeotrope distillate fraction and to obtain the organic iodine impurity in one or more lower boiling fractions.

2. A process as claimed in claim 1 wherein the organic iodine impurity consists essentially of methyl iodide.

3. A process for removing organic iodine compounds from acetaldehyde obtained as an homologization mixture of methanol which, in addition to acetaldehyde as the desired product and methyl iodide as the main impurity, essentially contains acetaldehyde dimethyl acetal, methanol, methyl acetate and water, which process comprises:
    (a) introducing the homologization mixture into the middle section of a column I at a temperature sufficient to completely vaporize the methyl acetate or its azeotropic mixture with methanol, but not the methanol,
    ($b_1$) feeding liquid aqueous acid, in counter-current to the rising vapors, into the top quarter of column I in order to split the acetaldehyde dimethyl acetal into acetaldehyde and methanol, or
    ($b_2$) instead of the aqueous acid, using only water and splitting the acetal by means of a solid acid ion exchanger,
    (c) taking off a vaporous mixture of methyl acetate and acetaldehyde at the top of column I and separating it into its components in a column II,
    (d) taking off a liquid mixture of methanol and water from the bottom quarter of column I and separating it into its components in a column III, and
    (e) removing some of the aqueous acid (embodiment $b_1$) obtained in the bottom of column I or removing some of the water (embodiment $b_2$) from the system with minor amounts of other products, and combining the remainder of this aqueous acid or of the water with the water obtained in the bottom of column III, and recycling the aqueous solution into the top quarter of column I, after addition of an acid, the separation of methyl acetate and acetaldehyde in process step (c) being carried out in the presence of a hydrocarbon with a boiling point, under atmospheric pressure, of from 25° to 55° C., and said column II being maintained under conditions of temperature and pressure sufficient for the acetaldehyde/hydrocarbon mixture to be taken off from the top of said column II, a fraction containing the iodine compound, methyl acetate and the hydrocarbon to be removed as a lateral take-off from said column II, and the methyl acetate fraction to be taken off as the bottom product from said column II.

4. A process for separating organic iodine compounds as an impurity from a crude acetaldehyde obtained by the homologization of methanol, using a catalyst system comprising carbonyl complexes of metals of Group VIII of the Periodic Table of the elements and iodine compounds as activators, which process comprises:
    subjecting said crude acetaldehyde to azeotropic distillation with a hydrocarbon which has a boiling point, under atmospheric pressure, of from 25° to 55° C., said distillation being carried out under conditions of temperature and pressure sufficient to obtain the purified acetaldehyde in the azeotrope distillate fraction and to obtain the organic iodine impurity in one or more lower boiling fractions.

5. A process as claimed in claim 4 wherein the organic iodine impurity consists essentially of methyl iodide.

6. A process as claimed in claim 1, 3 or 4 wherein methylbutane is used as the hydrocarbon.

* * * * *